US005585570A

United States Patent [19]

Raymond

[11] Patent Number: 5,585,570

[45] Date of Patent: Dec. 17, 1996

[54] RISING STEP-LOAD TEST APPARATUS

[75] Inventor: Louis Raymond, Newport Beach, Calif.

[73] Assignee: LRA Laboratories, Inc., Newport Beach, Calif.

[21] Appl. No.: 321,396

[22] Filed: Oct. 12, 1994

[51] Int. Cl.$^6$ .................................................. G01N 3/10

[52] U.S. Cl. ................................ 73/851; 73/799; 73/816; 73/853; 73/856

[58] Field of Search ............................ 73/788, 795, 799, 73/812, 816, 819, 821, 834, 835, 840, 845, 846, 849, 851, 853, 854, 856, 857

[56] References Cited

U.S. PATENT DOCUMENTS

| | | | |
|---|---|---|---|
| 3,643,496 | 2/1972 | Zajic | 73/816 |
| 3,965,729 | 6/1976 | King, Jr. | 73/799 |
| 4,002,061 | 1/1977 | Smith et al. | 73/812 |
| 4,305,300 | 12/1981 | Petersen et al. | 73/788 |
| 4,335,615 | 6/1982 | Kalfa et al. | 73/799 |
| 4,730,498 | 3/1988 | Blanch | 73/856 |
| 4,735,093 | 4/1988 | Burchill et al. | 73/854 |
| 4,836,029 | 6/1989 | Skala et al. | 73/799 |
| 5,005,423 | 4/1991 | Poormon | 73/799 |
| 5,184,517 | 2/1993 | Kelzer | 73/851 |
| 5,277,069 | 1/1994 | Cussac et al. | 73/853 |
| 5,425,276 | 6/1995 | Gram et al. | 73/816 |

OTHER PUBLICATIONS

Raymond, Louis Dr., "Hydrogen Embrittlement of Fasteners: Problems and Solutions", *American Fastener Journal*, May/Jun. 1993.

Raymond, L. et al., "Accelerated, Low-Cost Test Method for Measuring the Susceptibility of Hy-Steels to Hydrogen Embrittlement", pp. 477-480, 1982.

Tyler, P. S. et al., "Investigation of the Conditions for Crack Propagation and Arrest Under Cathodic Polarization by Rising Step Load Bend Testing", *Corrosion*, vol. 47, No. 2, pp. 82-87, Feb. 1991.

Movich, R. C., "Notched Bar-Bending Test", *Hydrogen Embrittlement Testing, ASTM STP 543*, American Society for Testing and Materials, pp. 64-73, 1974.

*Primary Examiner*—Richard Chilcot
*Assistant Examiner*—Eric S. McCall
*Attorney, Agent, or Firm*—Knobbe, Martens, Olson & Bear

[57] ABSTRACT

A rising step-load test apparatus for subjecting the notched region of a fracture specimen to tension by applying four-point bending to the specimen, and having an adaptor that can fit into the test apparatus in four-point bending and convert the bending load to an axial tensile load on a second specimen for which the adaptor serves as a fixture. The test apparatus applies four-point bending to either the fracture specimen or the adaptor through two oppositely situated simple supports at one end of the fracture specimen or adaptor and two other oppositely situated simple supports at the other end of the fracture specimen or adaptor. The adaptor employs two pivotally attached linking members attached to the two ends of the second specimen to transfer a pure axial tension to the second specimen for testing in axial-tension mode. A chemical bath is provided for an accelerated test of hydrogen embrittlement.

18 Claims, 7 Drawing Sheets

RISING STEP-LOAD TEST APPARATUS

STATEMENT OF GOVERNMENT INTEREST

This invention was made with Government support under a Small Business Innovation Research grant, awarded by the United States Navy. The Government has certain rights in this invention.

FIELD OF THE INVENTION

The present invention relates to a fracture toughness test apparatus and, more specifically, to a rising step-load test apparatus that applies four point bending to a test sample or fixture.

BACKGROUND OF THE INVENTION

Concern with stress corrosion cracking in high-strength steels and steel weldments has prompted the development of laboratory tests for hydrogen embrittlement of these steels and weldments. Early tests impose a static tensile load on a notched tensile coupon since hydrogen embrittlement failure occurs under a static tensile load for an extended period of time as hydrogen migrates to areas of stress concentration and causes brittle fracture. A chemical bath can be used to induce absorption of hydrogen into the material. The time required for failure of the steel or weldment depends on the absorbed hydrogen concentration, the magnitude of the stress concentration, and the magnitude of the applied stress.

One early apparatus employs a stress-rupture machine which loads a notched tensile coupon statically in tension at 75 percent of its ultimate strength until failure occurs or 200 hours have elapsed. Clear disadvantages of this type of tensile testing apparatus include the high cost of a stress rupture machine and the need to prepare test coupons with threads or shoulders for gripping on the machine for tensile loading.

To overcome these problems, researchers have developed a method whereby a notched coupon is loaded in tension by bending. Because the coupon is not loaded axially in tension, no threads or shoulders for gripping are necessary. The coupon is simply slipped into the testing device for loading. In addition, because the load requirement is lower, the cost of such a testing device is usually a fraction of the cost of a stress rupture machine.

In the article, L. Raymond & W. R. Crumley, "Accelerated, Low-Cost Test Method for Measuring the Susceptibility of HY-Steels to Hydrogen Embrittlement," American Society for Metals, 1982, is shown a loading frame that loads a notched sample in tension by bending it with a pair of loading arms. The sample is notched at the mid-section and clamped at both ends by the pair of loading arms. The loading arms are pivoted at the bottom and rotate as loading is applied by turning the instrumented bolt at the top end of the loading arms, bringing them together. This effects a bending moment on the clamped sample, causing the notch to open in tension. A rising step-load procedure is used to load the sample with increasing stress-to-failure so that the susceptibility to hydrogen assisted cracking can be indexed with respect to the failure load.

Although this type of loading frame has numerous advantageous over the tensile testing apparatus, it also has certain disadvantages. The load transfer between the two loading arms and the sample is poor due to the inherent problems of the loading frame linkage. Each of the two loading arms is pivoted at the bottom. For each arm, there are top and bottom sections connected by screws. The bottom section is pivoted at the lower end and has a slot for holding the sample horizontally at the upper end. To place the sample in position for loading, the two top sections of the loading arms are first removed. After the sample is placed horizontally in the slots provided by the bottom sections of the two loading arms, the top sections are placed on top to hold the sample in place, using a set of screws that penetrate through the bottom sections into the top sections; in other words, the sample is clamped between the top and bottom sections. As loading is applied by turning the instrumented bolt and a bending moment is transferred to the sample, a large amount of mechanical slop can result in the linkage due to the many separate components in the overall loading frame linkage through which the load is transferred. This can be caused by bolt misalignment, and friction and slippage at various contact surfaces within the linkage of the loading frame, leading to false or inaccurate load readings.

It is intended that the apparatus apply four-point bending to the sample. However, the connections between the pair of loading arms and the sample are neither perfectly fixed clamps nor simple supports at four points. This causes slippage between the sample and the loading arms, resulting in a loading mode that is not truly a four-point bending. In addition, this slippage leads to inefficient load transfer to the sample. Consequently, false load readings and possible changes in sample displacement may result.

The placement of instrumentation for load measurement further contributes to the inaccuracy in load readings. The load measurement is taken at the instrumented bolt, which is far removed from the sample. Inaccuracy in load readings results from the large separation between the bolt and the sample and the inefficient load transfer due to mechanical slop and slippage between the point of measurement and location of the sample.

In this type of apparatus, sensitive crack detection in the test sample requires accurate load measurement. Further, when the sample is tested under constant displacement, any movement of the sample will compromise the integrity of the measured data. Movement can result from sample slippage, temperature fluctuations, and bending or relaxation in the test apparatus. As described above, these problems are present in this loading structure, creating problems of inaccuracies in load and displacement measurements.

Furthermore, the process of installing the sample into the loading frame is rather complicated and cumbersome because one must loosen the screws and remove the top sections of the two loading arms and the instrumented bolt structure, which constitute the bulk of the weight of the apparatus. After the sample is placed in the slots of the two bottom sections, the top sections of the loading arms and the bolt structure are turned over to be clamped onto the sample. Because the loading frame must be rigid and substantial in weight, it is generally very heavy, especially for larger samples, making it difficult or impractical to deposit and remove samples. This also restricts the size of samples that can practically be tested with this loading frame. The fact that much of the positioning and adjustment required in depositing and removing the sample is performed inside the chemical bath further complicates and slows down the procedure.

SUMMARY OF THE INVENTION

The present test apparatus alleviates the above described significant disadvantages of the prior art devices by providing a linkage system that subjects the notched sample to four-point bending and efficiently transfers the load to the sample. Much of the inaccuracy in load measurement is eliminated. The apparatus is set up in such a way that load measurement can take place in close proximity to the sample, for accurate reading. The design also makes the process of installing the sample into the loading frame, and removing it, fast and easy.

The testing apparatus includes two holders for the sample, a first holder that is fixed with respect to a rigid frame and a second holder that is fixed to one end of a crossbeam that has two ends. The other end of the crossbeam is attached to one end of an actuator, which has a second end attached to the rigid frame.

The first holder makes contact with the sample near the sample's first end through two supports that are disposed at opposite sides of the sample. These supports create two lines of contact that are parallel to one another and perpendicular to the sample's longitudinal axis. Similarly, the second holder makes contact with the sample near the sample's second end through two supports that are disposed at opposite sides of the sample. The supports create two additional lines of contact that are parallel to one another and perpendicular to the sample's longitudinal axis. Each support is a simple support that transmits only forces that are perpendicular to the side of the sample in contact with the support, but no bending moments. As the actuator is activated, the load is transferred through the crossbeam to the specimen via the two supports at the second holder. This causes reaction forces at the two other supports at the first holder fixed to the rigid frame. Thus, the sample is loaded in true four-point bending via the four simple supports.

The four-point bending mode of loading via simple supports is advantageous because it eliminates the friction and slippage that cause inaccuracies in load and displacement measurements in loading configurations such as an imperfect clamp. The load transfer from the actuator to the sample is also much more efficient through a single crossbeam, without the mechanical slop that is present in the above-described prior-art device with multiple points of connections between numerous components and many changes for misalignment, slippage, and friction.

The actuator can simply be a linear actuator that moves along one dimension. In a preferred embodiment, the actuator comprises a stepper motor coupled to a drive shaft coupled to a drive bearing. The stepper motor also makes possible the rising step-load test procedure whereby rising step loads are used to accelerate the fracture test.

Another important feature of the preferred embodiment of the test apparatus is that it makes the deposit and removal of the sample fast and easy because only the crossbeam need be moved. The procedure is further simplified by having the crossbeam rotatably attached to the linear actuator so that the crossbeam may rotate between an open position and a closed position. The old sample can be easily removed by rotating the crossbeam to an open position. A new sample can be quickly inserted in the first holder fixed to the frame and set in place by lowering the crossbeam and placing the second holder on top of the sample.

The apparatus also provides a convenient location for a chemical bath for the sample if one is desired. To achieve the effect of hydrogen embrittlement, the entire sample need not be submerged in the bath. The bath only needs to cover the region of stress concentration such as a notch area. In the preferred embodiment, the bath is attached to the frame and located above the first holder and below the second holder.

In addition, the load can be conveniently measured at a number of locations, including the frame, linear actuator, crossbeam, or sample. In the preferred embodiment, a strain gauge is used and located at the crossbeam adjacent the second holder for the sample. Additional strain gauges can also be used.

Yet another significant feature of the present test apparatus is that an adaptor can be used to convert a bending test apparatus, such as the one just described, from applying a bending moment to a first sample into applying a pure tensile load axially to a second sample. The adaptor fits into the first and second holder in place of the first sample and serves as a fixture for the second sample, transferring a tensile load to it. The adaptor comprises two bending members and two linking members. The first holder makes line contacts with the first bending member at two simple supports on opposite sides and the second holder makes line contacts with the second bending member at two additional simple supports, creating a four-point bending load on the adaptor.

The second end of the first bending member has a first bearing surface at a distance $D_1$ from the centerline. At a distance $D_2$ from the centerline, opposite from the first bearing surface and near the second end of the first bending member, is pivotally attached the first linking member, which is also attached to the first end of the second sample. A second bearing surface is located at the second end of the second bending member at a distance $D_3$ from the centerline and bears against the first bearing surface of the first bending member. A second linking member is pivotally attached to the second bending member near the second bending member's second end, at a distance $D_4$ from the centerline opposite the second bearing surface. The second sample is attached at its second end to the second linking member. Preferably, the first and second bearing surfaces of two bending members are rounded and bear against a rod instead of against one another.

To effect a tensile load axially on the second sample, a test apparatus is used comprising a rigid frame, a first holder fixed to the frame, a linear actuator attached at one end to the frame, a crossbeam attached at one end to the other end of the linear actuator, a second holder fixed with respect to the crossbeam, and the adaptor as described above. The first end of the first bending member is received into the first holder; and the first end of the second bending member is received into the second holder. As the loading frame applies bending moments to the two bending members via four-point bending, the bearing surfaces of the two bending members bear against one another, or a rod in compression, and an axially tensile force is exerted on the second sample through the two linking members pivotally attached to the two bending members.

The present test apparatus can be used to test a sample or fixture under constant displacement control, causing crack growth to occur at a constant stress intensity on fracture samples. This enables the measurement of the threshold stress intensity that induces crack growth on a test sample, resulting in an accelerated method to measure the threshold value of the material for the onset of stress corrosion cracking in air or a liquid environment under potentiostatic control.

BRIEF DESCRIPTION OF THE DRAWINGS

These and other advantages of the present invention are best understood with reference to the drawings, in which.

DETAILED DESCRIPTION OF THE PREFERRED EMBODIMENT

Figure 1:
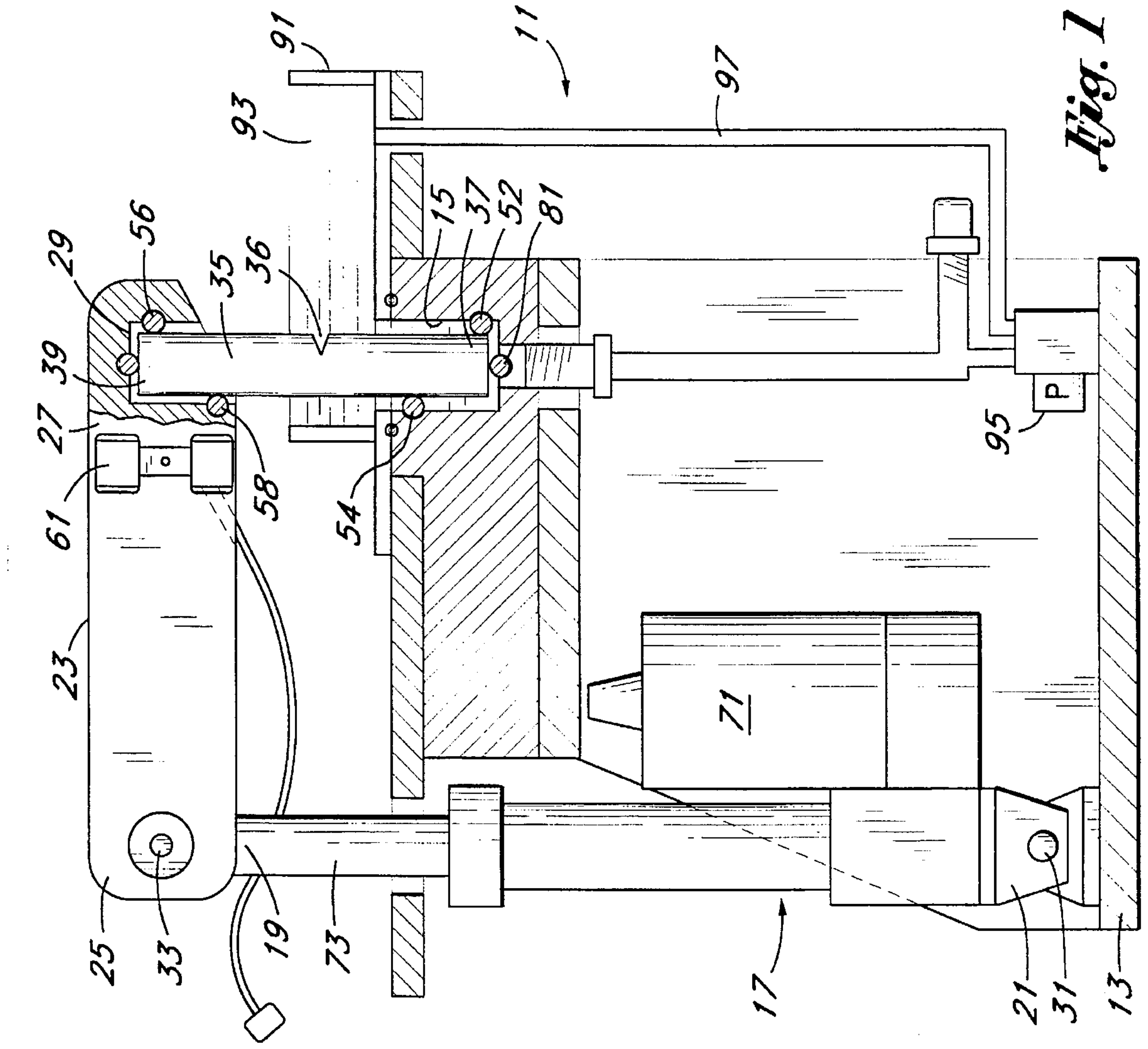
FIG. 1 is a partially cross-sectioned front view of the rising step load test apparatus with a first sample subjected to four-point bending according to a preferred embodiment.

As shown in FIG. 1, the preferred embodiment comprises a test apparatus 11 including a rigid frame 13, a first holder 15 fixed with respect to frame 13, an actuator 17 having a first end 19 and a second end 21, a crossbeam 23 having a first end 25 and a second end 27, and a second holder 29 fixed with respect to crossbeam 23.

The actuator 17 has its second end 21 attached to the frame 13 and its first end 19 attached to the first end 25 of the crossbeam 23. The manner of attachment can take on various forms. In the preferred embodiment shown in FIG. 1 and the side view in FIG. 2, the connection between the frame 13 and actuator 17 is secured by a pin 31, mounted in bearings to allow rotation of the actuator 17 with respect to the frame 33. Another pin 33, mounted in bearings, connects the actuator 17 and the crossbeam 23 to permit rotation between the actuator 17 and crossbeam 23. As will be discussed later, this type of connection allowing rotational movement facilitates the fast and easy deposit and removal of test samples, and minimizes the friction and slippage inherent in earlier designs.

A first sample 35 is located between the first holder 15 and second holder 29. The sample 35 has a first end 37, a second end 39, and a notch 36 in between the two ends, 37 and 39. A longitudinal axis 41 is indicated along the length of the sample 35. The four points of loading on sample 35 to effect four-point bending are applied to opposite sides of sample 35, a first side 43 and a second side 45. In the preferred embodiment of FIG. 1, the sample 35 has a rectangular or square cross section and side 43 and side 45 are parallel to the longitudinal axis 41.

Figure 3:
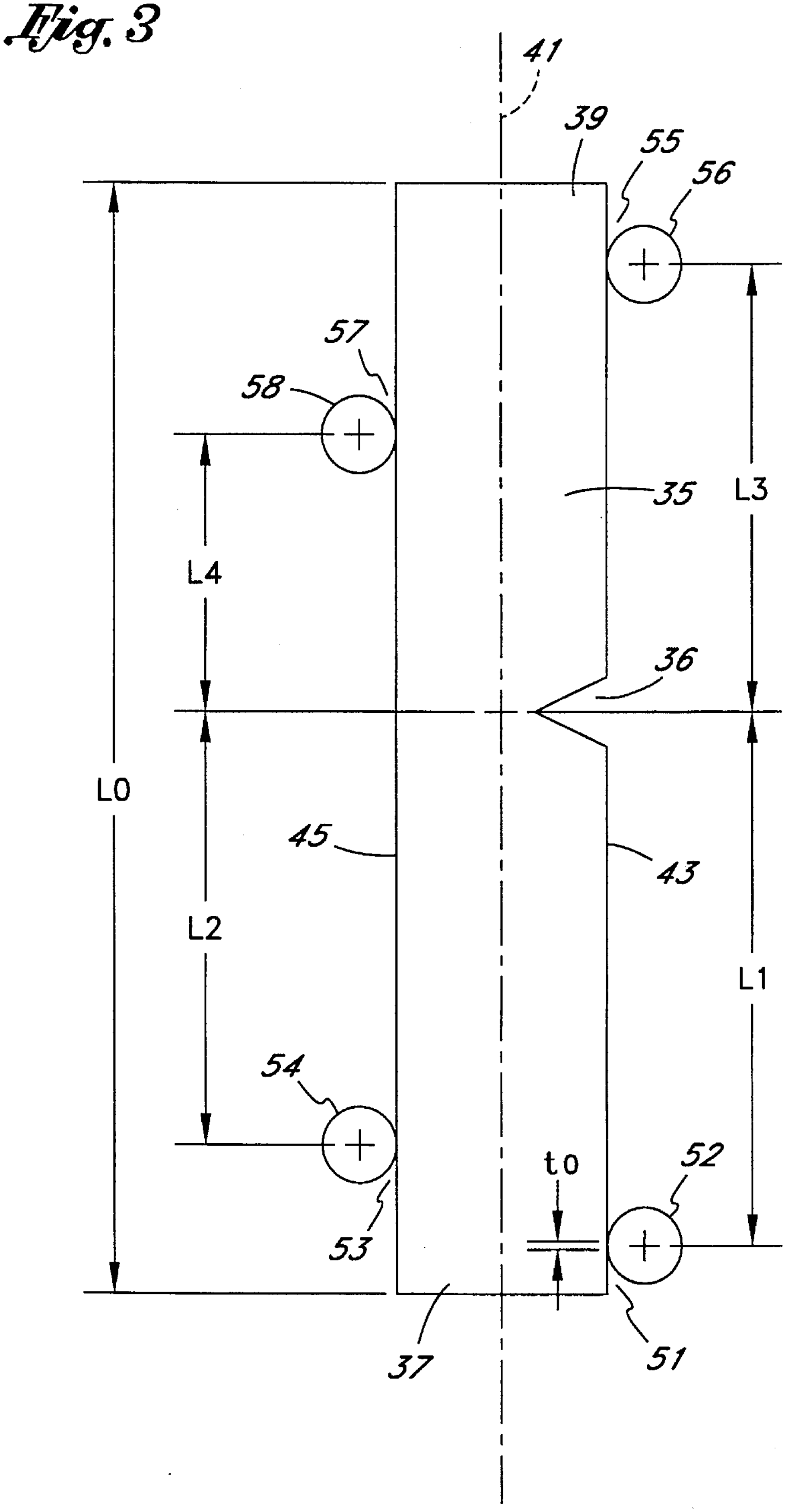
FIG. 3 is a first sample showing the four-point bending mode of loading.

As best seen in FIG. 3, the first holder 15 makes contact with the first side 43 at a first support surface 51 near the first end 37 through a first support 52, which contact is actually a line contact in a direction perpendicular to the longitudinal axis 41. A line contact can be formed by providing a round cylindrical support to bear against the first side 43. On the opposite side, the first holder 15 makes a line contact with the second side 45 at a second support surface 53 through a second support 54, which support surface 53 is parallel with the first support surface 51. Near the second end 39 of the sample 35, the second holder 29 makes line contact with the first side 43 at a third support surface 55 through a third support 56, and with the second side 45 at a fourth support surface 57 near the second end 39 through a fourth support 58, which support surfaces 55 and 57 are both parallel with the other support surfaces 51 and 53. Therefore, the four-point bending is effected by four simple supports 52, 54, 45, and 58 that form four line-contact support surfaces 51, 53, 55, and 57 for the sample 35.

It will be appreciated that the test apparatus 11 can be oriented in a number of ways. In the preferred embodiment of FIG. 1, the apparatus 11 is set up to orient the sample 35 with its longitudinal axis 41 in the vertical direction such that the first end 37 is substantially directly below the second end 39. Gravity causes the first end 37 of sample 35 to rest on the first holder 15 at a stop 81. This contact does not affect the four-point bending configuration. To minimize friction when the sample 35 is subject to bending, the stop 81 forms a line contact with the sample 35. This can be achieved using a round cylindrical support for the stop 81. Friction can be further reduced if the stop 81 makes a rolling contact with sample 35.

Figure 4:
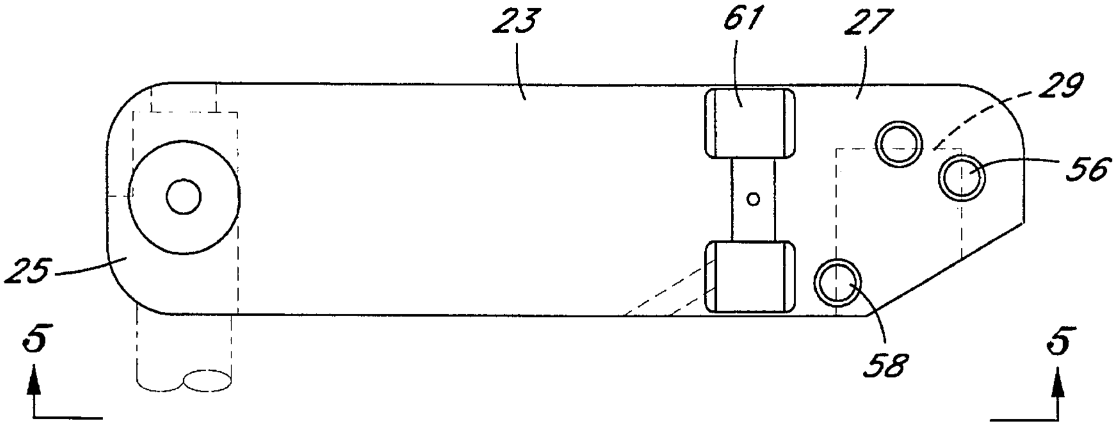
FIG. 4 is a front view of the crossbeam member of the test apparatus of FIG. 1 showing the details of the second holder fixed at one end of the crossbeam and the connection with the actuator at the other end of the crossbeam.
Figure 5:
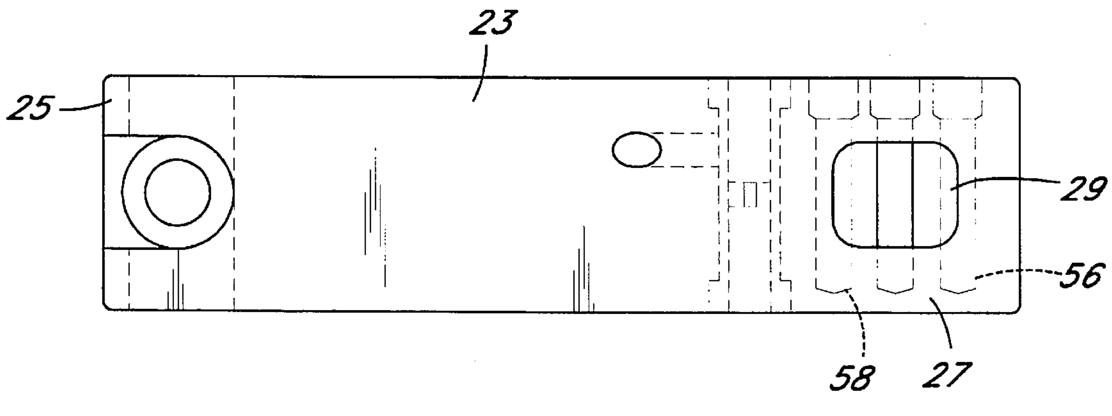
FIG. 5 is a side view of the crossbeam of FIG. 4.

Measurement of the applied loading can be accomplished by attaching instrumentation to the test apparatus such as the frame 13, actuator 17, or crossbeam 23, or to the sample 35. A strain gauge is a common device for measuring the strain from which the load can be reduced. In the preferred embodiment in FIG. 1, a strain gauge 61 is located in the crossbeam 23. More details of the crossbeam 23 are shown in FIGS. 4 & 5, including the strain gauge 61. While mounting a strain gauge on the sample 35 would provide a better measure of loading on the sample 35, it is not as convenient and economical as having one permanently mounted on the test apparatus, such as on the crossbeam 23. To obtain good load measurement, the strain gauge 61 is placed adjacent the second holder 29, so that it is very close to the sample 35.

In addition, more than one strain gauge can be used. For example, a second strain gauge, not shown, can be attached to the actuator 17 to measure the strain in that second location.

Another feature shown in FIG. 1 is a chemical bath 91 containing bath solution 93 in which the sample 35 is submerged. There can be provided a circulation pump 95 that circulates the solution 93 through circulation line 97. This process ensures that the chemical concentration in the bath solution 93 remains uniform and approximately constant.

As best seen in FIG. 3, the notch 36 is on the first side 43 of sample 35 between the first end 37 and second end 39. To efficiently effect a bending moment on sample 35 such that it subjects the notch area to tension, the distance $L_1$ between the notch 36 and first support surface 51 should be larger than the distance $L_2$ between the notch 36 and second support surface 53 along the longitudinal axis 41. The moment arm near the first end 37 is the difference between $L_1$ and $L_2$. Similarly, the distance $L_3$ between the notch 36 and third support surface 55 should generally be greater than the distance $L_4$ between notch 36 and fourth support surface 57, forming a moment arm for the second end 39 of the difference between $L_3$ and $L_4$. For structural efficiency and stability, $L_1$ can be made equal to $L_3$ and $L_2$ equal to $L_4$. Furthermore, the notch 36 can be placed in the middle of the sample 35 between the first end 37 and second end 39 such that the four-point loading at support surfaces 51, 53, 55, and 57 is symmetric with respect to the middle of the sample 35.

As seen in FIG. 3, the preferred embodiment has line-contact simple supports for the sample 35 such that only forces perpendicular to the first side 43 or second side 45 are transmitted to the sample 35. No complex bending moments or other forces are applied to the sample 35, in contrast with the case of a clamped or imperfectly clamped support. Ideally, a line contact has zero thickness so that a support transmits only a normal force perpendicular to the side in contact with the support. This creates what is known as a simple support because no bending moments or forces parallel to the side are transferred. In reality, the support surface will have a finite thickness, $t_0$, as shown in FIG. 3. As long as this thickness is small relative to the specimen length, $L_0$, the support surface is essentially a line contact and the support provides essentially a simple support for the specimen 35. It will be appreciated that a support surface with a thickness that is an order of magnitude smaller (i.e., $t_0<0.1\ L_0$) represents a substantial improvement over the prior-art clamped surface. Of course, further reduction of the line contact thickness $t_0$ is preferable; a thickness of $t_0<0.01\ L_0$ is achievable if the support surfaces and sample are sufficiently hard.

This simple form of loading facilitates efficient load transfer to the sample 35 and accurate readings of actual forces on the sample 35. There is less likelihood of slippage and friction because the area of contact is much smaller than that of a clamped surface. Even if there is slippage and friction, the friction will be negligibly small due to the small contact area. Furthermore, the loading will not change materially because the moment arm between the two opposite simple supports remains fixed, thus maintaining the same applied moment on the sample 35. Other cylindrical shapes than a round cylinder can be employed for the simple support 52, 54, 56, or 58 to form a line contact. However, a round cylinder is preferable because it provides a rolling contact when the specimen 35 deforms in bending, further reducing friction and slippage. It will be appreciated that a line contact is preferred to a point contact because of the stability of support and loading provided to the sample 35.

Therefore, the sample 35 fits tightly into the supports 52, 54, 56, and 58 provided by the first and second holders, 15 and 29. The line contacts at the four simple support surfaces 52, 53, 55, and 57 eliminate the mechanical slop present in the prior-art clamped loading design. As a result, the four-point bending configuration transfers loads to the sample 35 much more efficiently and the readings on the forces applied to the sample 35 and displacements are more accurate. This also facilitates accurate analytical modeling.

Figure 6:
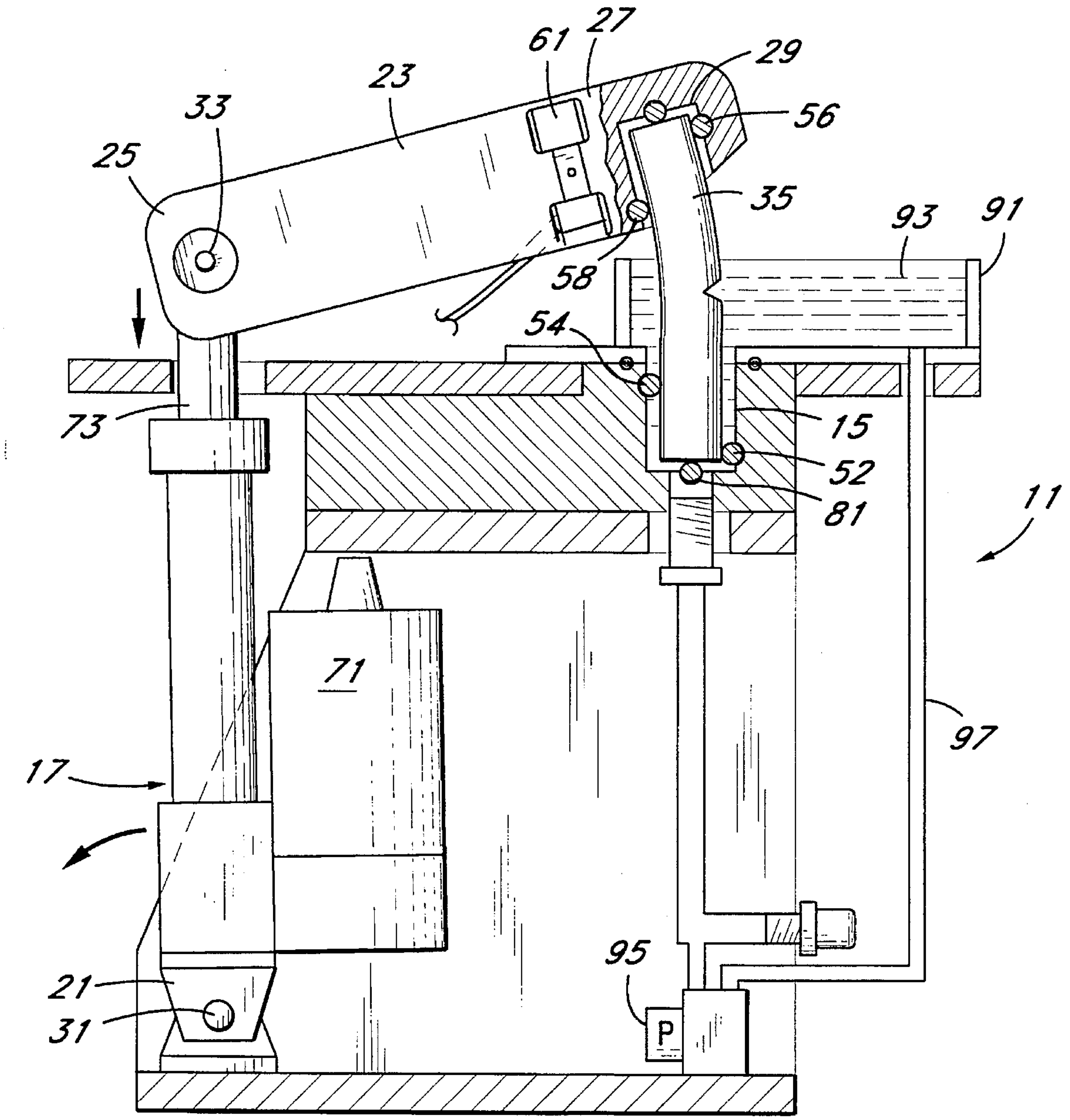
FIG. 6 is a partially cross-sectioned front view of the rising step load test apparatus of FIG. 1 during four-point loading of the sample.

The actuator 17 in FIG. 1 can be any device, manual or automatic, that moves the crossbeam 23 which in turn transfers the load to the sample 35 through the second holder 29. A linear actuator can be used simply to provide a linear motion along its two ends, 19 and 21. In the embodiment of FIG. 1, the linear actuator 17 comprises a stepper motor 71 coupled to a drive shaft and bearing (not shown), which are in turn coupled to a drive rod 73. The motor 71 moves the rod 73 in a linear direction, in this case up or down. As the drive rod 73 is driven downward, the first end 19 of the actuator 17 is brought closer to the second end 21. As seen in FIG. 6, because of the rotational attachment between the linear actuator 17 and the frame 13 at the actuator's second end 31, this linear motion causes the linear actuator 17 to effect a bending moment on sample 35 through the four points of loading, which tends to open the notch 36. (As will be appreciated, during this process there is some incidental rotation of the linear actuator 17 in a counter-clockwise direction and moving of the crossbeam 23 to the left.) The stepper motor is capable of providing step loads to the drive shaft, which is an important feature for testing with increasing step-loads.

The accurate measurement of the load applied to the sample 35, and the ability to impose different displacements in steps and maintain the displacement constant at each step, are paramount to accurate and efficient crack initiation detection. The present test apparatus 11 of FIG. 1 provides a single crossbeam 23 that is designed with a geometry to minimize deflection and maximum stress sensitivity. This facilitates use of a Wheatstone bridge to measure stress within the crossbeam 23. The Wheatstone bridge is an accurate method of load measurement because it eliminates false loads due to temperature and humidity variations. The direct mechanical linkage of the test apparatus 11 also enables more accurate load measurement by eliminating areas of friction, slippage, and bending that could lead to false variations in load measurement on the sample 35.

In utilizing the chemical bath 91 for testing involving hydrogen embrittlement, any bath solution 93 that will induce absorption of hydrogen into the sample 35 can be used. For example, a NaCl solution with a cathodic potential is commonly used. A 3.5% NaCl solution can be used to simulate sea water; the cathodical potential of −1.2 volts will simulate the extreme condition of sacrificial anodic protection generally found on a ship hull.

The notch 36 of sample 35 should be submerged in the bath solution 93 so that hydrogen can attack the stress concentration area at the notch 36. Therefore, it is not necessary to submerge the entire sample 35. In fact, it is more efficient to design a bath that does not cover more of the sample 35 than necessary. In the preferred embodiment of FIG. 1, the bath solution 93 covers just enough of the sample 35 to include the notch 36.

As shown in FIG. 1, the rigid frame 13 provides a convenient structure to which the chemical bath 91 can be securely attached. Nothing needs to be moved to fill the bath 91 with solution 93. To submerge the notch 36 of sample 35, the bath 91 is located between the first holder 15 and second holder 29. In the preferred embodiment of FIG. 1 in which the sample 35 is vertically disposed, the bath 91 is above the first holder 15 and below the second holder 29.

As seen in the preferred embodiment of FIG. 1, the first holder 15 defines an upwardly facing insertable opening so that the sample 35 can be easily deposited in the test apparatus by inserting the first end 37 into the first holder 15. The second end 39 of sample 35 also fits easily into the downwardly facing insertable second holder 29 to secure sample 35 for loading.

This configuration makes fast and easy the deposit and removal of sample 35 because only the crossbeam 23 which is fixedly attached to the second holder 29 need be moved. There is no need to turn the entire load frame over as in the prior art. In addition, because there is no need to submerge tools into the bath solution 93 to disassemble and reassemble components, potential contamination of solution 93 is eliminated and other safety precautions for working inside the chemical solution 93 are unnecessary.

Figure 2:
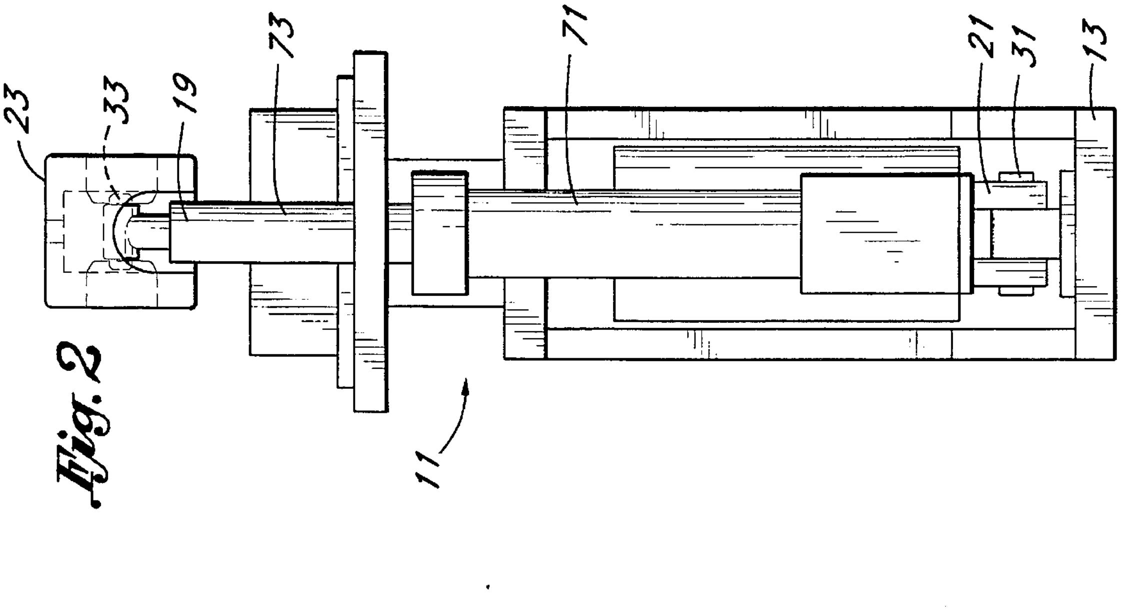
FIG. 2 is a side view of the test apparatus of FIG. 1.

To simplify the procedure even further, the crossbeam 23 is rotatably attached at its first end 25 to the first end 19 of the actuator 17. As shown in FIGS. 1 and 2, a pin 33 can be used for such a connection. As best seen in FIG. 6, the crossbeam 23 is rotatable between an open position and a closed position. To deposit or remove the sample, the crossbeam 23 is easily rotated to the open position, and then back to the closed position. There is no need to turn any screws or replace any fasteners, nor is there need to disassemble and reassemble any structure. The rotatable attachment also makes it easy to lift the crossbeam 23 to its open position by applying a relatively small force at its second end 27. The procedure is fast and saves time.

In addition, the loads applied to the sample 35 are restricted by the size and strength of the test apparatus 11. A larger sample would require a test apparatus with larger and stronger components. Without the efficient way or moving the crossbeam 23 to deposit and remove the sample 35, the procedure to carry out the testing can be very difficult and infeasible, as is the case in the prior-art apparatus. Thus, the current test apparatus 11 allows for a much larger range of loading forces and consequently a much larger range of sample sizes.

Figure 7:
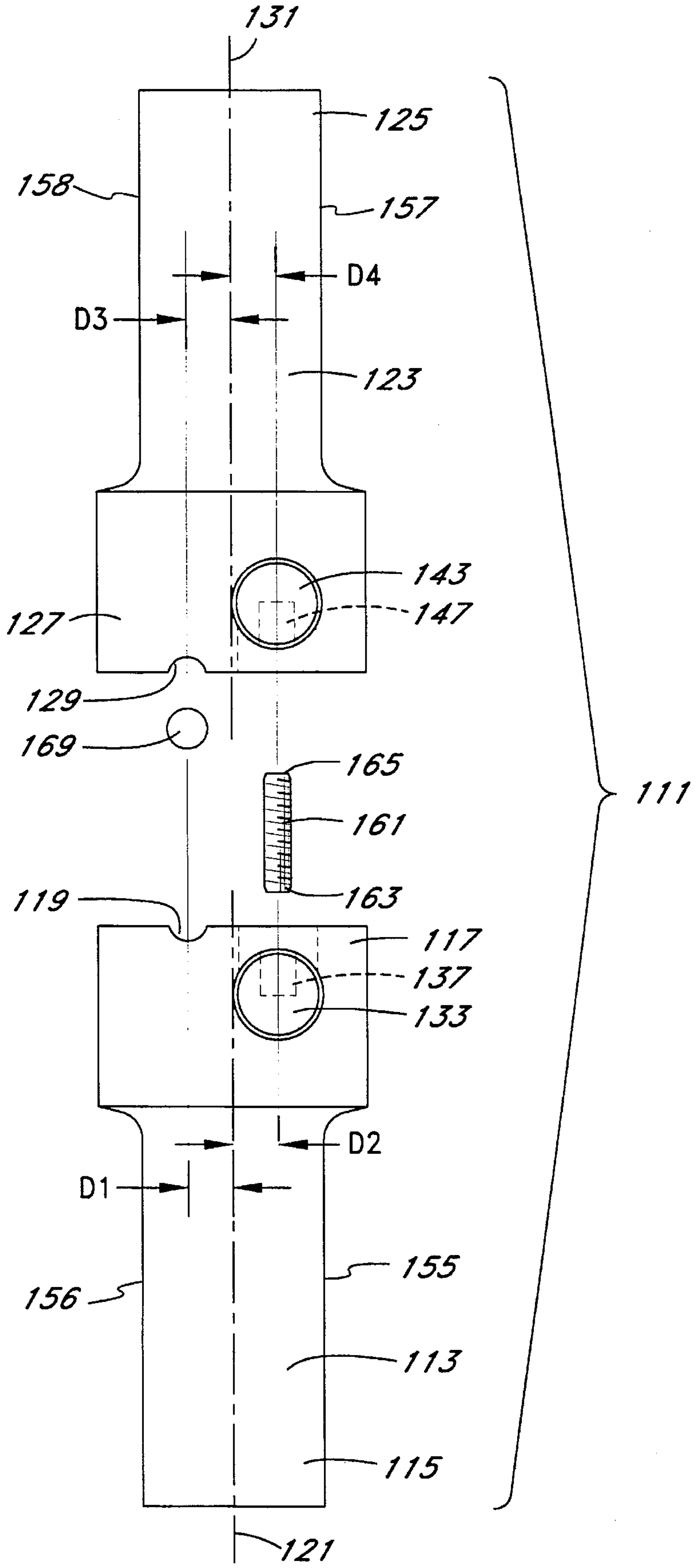
FIG. 7 is a front view of the adaptor and second sample according to a preferred embodiment.
Figure 8:
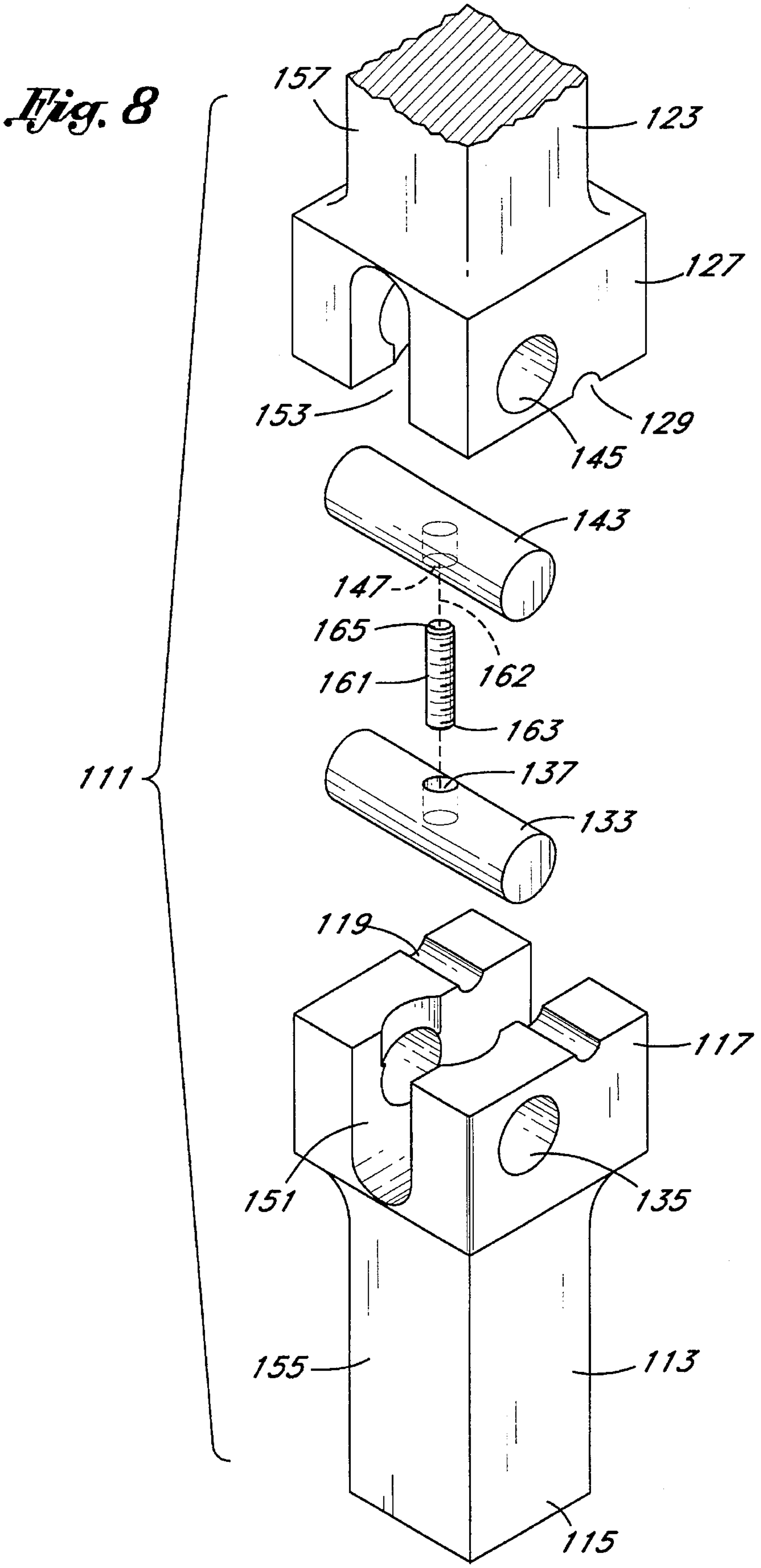
FIG. 8 is an exploded perspective view of the adaptor and second sample of FIG. 7.
Figure 9:
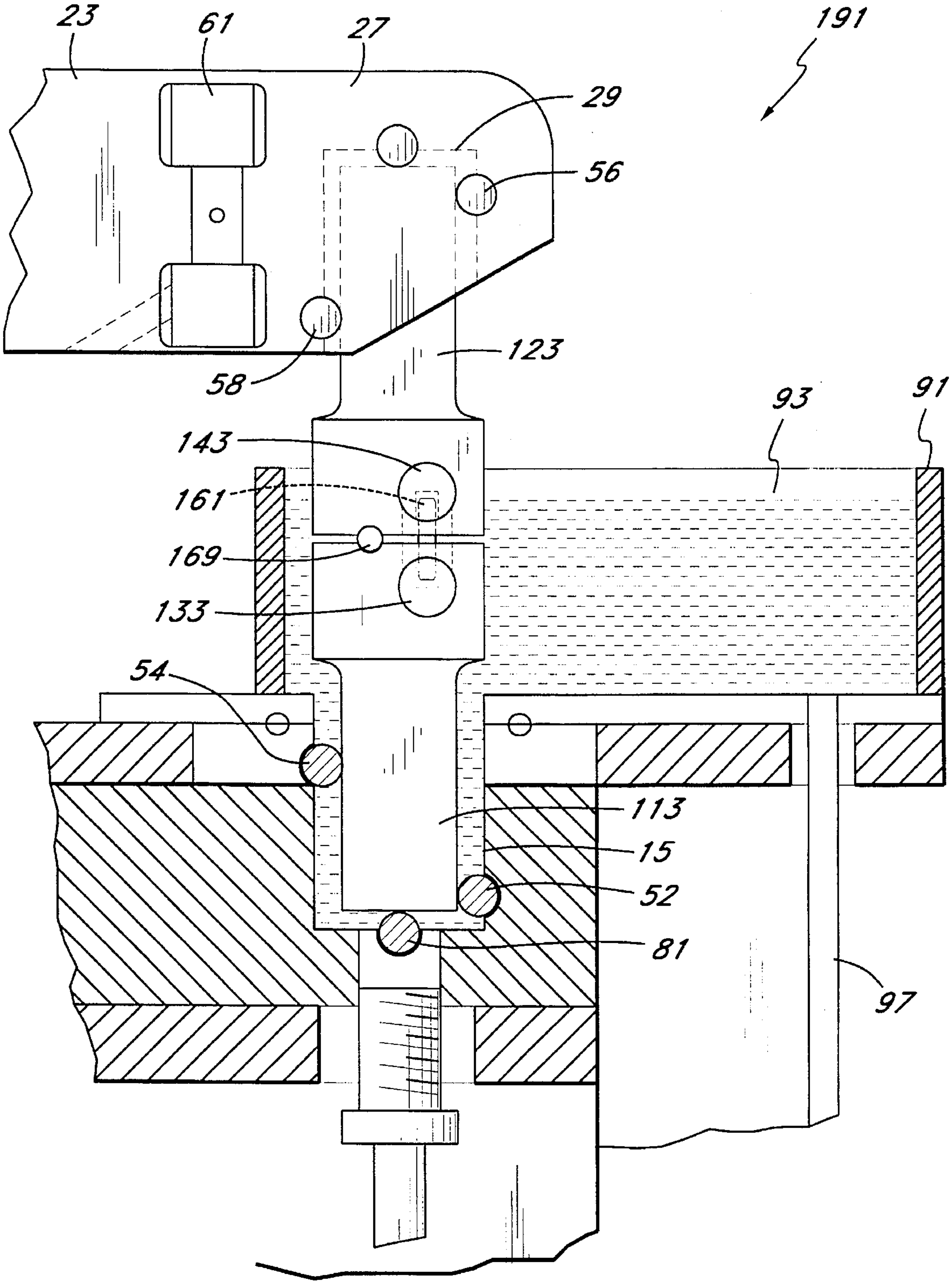
FIG. 9 is a fragmentary cross-section view of the adaptor and second sample of FIG. 7 assembled in a rising step-load test apparatus according to a preferred embodiment.

Another significant feature of the test apparatus in the present invention is that an adaptor 111 as shown in FIG. 7 can be used to convert the test apparatus 11 from testing a first sample 35 in bending into testing a second sample 161 in axial tension. Serving as a fixture for the second sample 161, the adaptor 111 comprises a first bending member 113, a second bending member 123, a first linking member 133, and a second linking member 143. FIG. 8 provides an exploded perspective view of the adaptor 111 and second sample 161. FIG. 9 shows a fragmentary cross-section view of a second test apparatus 191 utilizing the adaptor 111.

FIG. 7 is a front view of the adaptor 111 and second sample 161 according to a preferred embodiment. The first bending member 113 has a first end 115, a second end 117, a first side 155, a second side 156, and a first bearing surface 119 located at the second end 117 at a distance $D_1$ from its centerline 121. The second bending member 123 has a first end 125, a second end 127, a third side 157, a fourth side 158, and a second bearing surface 129 located at the second end at a distance $D_3$ from its centerline 131.

An exploded perspective view of the adaptor 111 and second sample 161 is shown in FIG. 8. The first linking member 133 is pivotally attached to the first bending member 113 near the first bending member's second end 117, at a distance $D_2$ from the centerline 121, opposite the first bearing surface 119. The second linking member 143 is pivotally attached to the second bending member 123 near the second bending member's second end 127, at a distance $D_4$ from the centerline 131, opposite the second bearing surface 129.

In the preferred embodiment of FIG. 8, the first linking member 133 is pivotally attached to the first bending member 113 by fitting into a first attachment cavity 135 provided in the first bending member 113. Similarly, the second linking member 143 is pivotally attached to the second bending member 123 by fitting into a second attachment cavity 145 provided in the second bending member 123. For cylindrical cavities 135 and 145 as shown in the preferred embodiment of FIG. 8, the linking members 133 and 143 are also cylindrical in shape.

The second sampling 161 is attached at its first end 163 to the first linking member 133, and is attached at its second end 164 to the second linking member 143. While the manner of attachment can take various forms, the preferred embodiment of FIG. 8 shows a third attachment cavity 137 provided in the first linking member 133 and a fourth attachment cavity 147 provided in the second linking member 143. The first end 163 of the second sample 161 has a shape complementary to the third attachment cavity 137; the second end 165 has a shape complementary to the fourth attachment cavity 147.

The second sample 161 can be of a variety of shapes. In FIG. 8 is shown an embodiment where the sample is in the form of an externally threaded shaft having a first end 163 and a second end 165. The first end 163 mates with an internally threaded third attachment cavity 137 or bore. The second end 165 is threadedly engaged with an internally threaded fourth attachment cavity 147 or bore. Alternatively, the second sample 161 could be in the shape of a screw. The first end 163 is the T-shaped end, which requires a complementary T-shaped slot.

To assemble the adaptor 111 with the second sample 161, the first linking member 133 is pivotally attached to the first bending member 113 at the first attachment cavity 135. The first end 163 of the second sample 161 is then attached to the first linking member 133 at the third attachment cavity 137. For a screw, the first end 163 is simply threaded into the third attachment cavity 137. This step is made possible by a first cutoff region 151 in the first bending member 113 that exposes the third attachment cavity 137 for the attachment of the first end 163 of the second sample 161.

Next, the second linking member 143 is pivotally attached to the second bending member 123 at the second attachment cavity 145. The last step is attaching the second end 165 of the second sample 161 to the second linking member 143 at the fourth attachment cavity 147. Similarly, this step is made possible by a second cutoff region 153 in the second bending member 123 that exposes the fourth attachment cavity 147 for the attachment of the second end 165 of the second sample 161. For the screw, this requires engaging the threaded second end 165 with the threaded fourth attachment cavity 147 to secure the second sample 161 to the adaptor 111 and complete the assembly.

The adaptor components are configured such that the first bearing surface 119 on the first bending member 113 bears against the second bearing surface 129 on the second bending member 123. In the preferred embodiment of FIG. 8, the bearing surfaces 119 and 129 are both rounded. Further, there is provided a rod 169 disposed between the first bearing surface 119 and the second bearing surface 129 such that they bear against the rod 169 rather than against one another.

When the bending members 113 and 123 are subject to a bending moment, the first and second bearing surfaces 119 and 129 bear against one another or against the rod 169 in compression. The side of the first bending member 113 opposite the centerline 121 from the first bearing surface 119 and the side of the second bending member 123 opposite the centerline 131 from the second bearing surface 129 are in tension. This tension is transferred from the first bending member 113 to the first linking member 133 and from the second bending member 123 to the second linking member 143. Located in between the first and second linking members 133 and 143 is the second sample 161 which is subsequently loaded in axial tension along its longitudinal axis 162.

The pivotal attachment between the first linking member 133 and the first bending member 113 and that between the second linking member 143 and the second bending member 123 are important in ensuring that a true axial tension is transferred to the second sample 161. As the bending load is applied to the adaptor 111, the bending members 113 and 123 rotate. If the linking members 133 and 143 were not pivotally attached, they would also be subjected to bending and would transfer the bending moment to the second sample 161. The pivotal attachments ensure that no bending moment is transferred from the bending members 113 and 123 to the second sample 161 through the linking members 133 and 143.

For structural efficiency and stability, the first and second bending members 113 and 123 are arranged by aligning their centerlines 121 and 131. Desirably, $D_1$ is equal to $D_3$ and $D_2$ is equal to $D_4$. In the preferred embodiment of FIG. 6, $D_1=D_2=D_3=D_4$. As a result, the centerlines 121 and 131 are aligned, the first and second bearing surfaces 119 and 129 are aligned, and the first and second linking members 133 and 143 are aligned and in symmetry with the first and second bearing surfaces 119 and 129 with respect to the centerlines 121 and 131. This preferred embodiment provides efficiency in transferring the tensile load to the second sample 161 and stability for the adaptor to avoid imbalance that may lead to slippage or friction. It also facilitates efficient analytical modeling.

It will be appreciated that a bending moment can be applied to the bending members 113 and 123 in various ways. One can employ an apparatus similar to the test apparatus 11 to apply four-point bending to the bending members 113 and 123. In that case, the first end 115 of the first bending member 113 can be close in shape and size to the first end 37 of sample 35 and the first end 125 of the second bending member 123 can be close in shape and size to the second end 39 of sample 35. In the preferred embodiment of FIG. 8, the first ends 115 and 125 are both rectangular in cross section.

As shown in FIG. 9, the components of the second test apparatus 191 are substantially similar to those of test apparatus 11, but with the addition of the adaptor 111. In place of the first sample 35 is the adaptor 111 serving as a fixture for the second sample 161. The first end 115 of the first bending member 113 is received within the first holder 15, and the first end 125 of the second bending member 123 is received within the second holder 29. The first bending member 113 makes contact with the first holder 15 at the first side 155 with the first support 52 of the first holder 15 and at the second side 156 with the second support 54 of the first holder 15, forming two lines of contact that are parallel to one another and perpendicular to the first bending member's centerline 121. The second bending member 123 makes contact with the second holder 29 at the third side 157 with the third support 56 of the second holder 29 and at the fourth side 158 with the fourth support 58 of the second holder 29, forming two additional lines of contact that are parallel to one another and perpendicular to the second bending member's centerline 131. As a result of these four lines of contact, the test apparatus 191 applies a bending moment on the adaptor 111 via four-point bending. As described above, this cause tensile forces to be transferred to the two linking members 133 and 143 of the adaptor 111, loading the second sample 161 in axial tension.

It will be appreciated that the adaptor 111 provides additional locations to mount one or more strain gages, not shown, to measure the load in close proximity to the second sample 161.

The current test apparatus 191 is ideally suited for testing hydrogen embrittlement of fasteners which are typically small in size. Since the onset of crack growth instead of complete rupture of the sample 161 is monitored, the test apparatus 191 provides an accelerated test by which one can quickly obtain dependable hydrogen embrittlement test results, often within 24 hours.

Thus, the test apparatus of the present invention provides an efficient linkage for loading and load transfer, eliminates inaccuracies in the application and measurement of load and displacement, and simplifies and expedites the testing procedures.

The present invention may be embodied in other specific forms without departing from its spirit or essential characteristics. The described embodiments are to be considered in all respects only as illustrative, and not restrictive. Further modifications may now suggest themselves to those skilled in the art. It is intended to include such modifications as fall within the scope of the appended claims so that all changes which come within the meaning and range of equivalency of the claims are to be embraced within their scope.

I claim:

1. An apparatus for detecting crack growth of a sample, said sample having first and second ends, a longitudinal axis, and first and second sides opposite one another and parallel to the longitudinal axis, said apparatus comprising:

a rigid frame;

a first holder fixed with respect to the frame, said first holder comprising two simple supports which are disposed to contact the opposing sides of the sample near the sample's first end, said two supports positioned and configured to contact the sample solely along two lines of contact which are parallel to one another and perpendicular to the sample's longitudinal axis;

a linear actuator having first and second ends, the second end attached to the frame;

a crossbeam having first and second ends, the first end of the crossbeam attached to the first end of the linear actuator;

a second holder fixed with respect to the crossbeam, said second holder comprising two simple supports which are disposed to contact the opposing sides of the sample near the sample's second end, said two supports positioned and configured to contact the sample solely along two lines of contact which are parallel to one another and perpendicular to the sample's longitudinal axis, the distance between said two supports along the sample's longitudinal axis defining a moment arm through which a bending load is applied to the sample by the crossbeam; and a strain gauge located on one of said frame, linear actuator, crossbeam, or sample.

2. The apparatus of claim 1, further comprising a chemical bath surrounding part of the sample.

3. The apparatus of claim 1, wherein the strain gauge is located within the crossbeam.

4. The apparatus of claim 1, wherein the strain gauge is located within the crossbeam adjacent the second holder.

5. The apparatus of claim 1, wherein the linear actuator is a stepper motor coupled to a drive shaft coupled to a drive bearing.

6. The apparatus of claim 1, further comprising a second strain gauge which measures the strain in the linear actuator.

7. The apparatus of claim 1, wherein the first and second holders hold the sample vertically, so that the sample's first end is substantially directly below the sample's second end.

8. An apparatus for detecting crack growth of a sample having first and second ends, said apparatus comprising:

a rigid frame;

a first holder defining a first upwardly facing opening through which the first end of the sample is insertable and retractable from above, said first holder fixed with respect to the frame and having simple supports that contact the first end of the sample;

a linear actuator having first and second ends, the second end attached to the frame;

a horizontal crossbeam having first and second ends, the first end of the crossbeam attached to the first end of the linear actuator;

a second holder defining a second opening through which the second end of the sample is insertable and retractable, said second holder fixed with respect to the crossbeam and having simple supports that contact the first end of the sample;

a chemical bath attached to the frame, located above the first holder and below the second holder; and a strain gauge located on one of said frame, linear actuator, crossbeam, or sample.

9. The apparatus of claim 8, wherein the first end of the crossbeam is rotatably attached to the first end of the linear actuator so that the crossbeam is rotatable between an open position and a closed position.

10. An apparatus for detecting crack growth of a sample having first and second ends, said apparatus comprising:

a rigid frame;

a first holder which has simple supports that hold the first end of the sample, said first holder fixed with respect to the frame;

a linear actuator having first and second ends, the second end attached to the frame;

a crossbeam having first and second ends, the first end of the crossbeam rotatably attached to the first end of the linear actuator so that the crossbeam may rotate between an open position and a closed position;

a second holder which has simple supports that hold the second end of the sample, said second holder fixed with respect to the crossbeam, wherein when the first end of the sample is placed in the first holder and the crossbeam is rotated into the closed position, the second holder closes around the second end of the sample and secures the sample between the crossbeam and the frame; and a strain gauge which measures the strain in the crossbeam.

11. The apparatus of claim 10, wherein the strain gauge is located within the crossbeam.

12. The apparatus of claim 10, wherein the strain gauge is located within the crossbeam adjacent the second holder.

13. An apparatus for detecting crack growth of a sample having first and second ends, said apparatus comprising:

a rigid frame;

an actuator connected to the frame;

a crossbeam connected to the actuator so that the actuator can move the crossbeam relative to the frame;

a first holder fixed with respect to the frame, said first holder holding the first end of the sample, and a second holder fixed with respect to the crossbeam, said second holder holding the second end of the sample, said first and second holders having four simple supports that place the sample in four-point bending when the crossbeam is moved relative to the frame; and a strain gauge which measures the strain in the crossbeam.

14. The apparatus of claim 8, wherein the first holder has a first stop that contacts the sample at the first end surface, carrying the weight thereof, a first essentially simple support that contacts a first vertical surface of the sample, and a second essentially simple support that contacts a second vertical surface of the sample opposite the first vertical surface.

15. The apparatus of claim 14, wherein the second holder has a second stop that contacts the sample at the second end surface, a third essentially simple support that contacts the first vertical surface of the sample, and a fourth essentially simple support that contacts the second vertical surface of the sample.

16. The apparatus of claim 15, wherein the first stop and second stop are essentially simple supports.

17. The apparatus 16, wherein the essentially simple supports are cylindrical supports that hold the sample with essentially line contacts.

18. The apparatus of 17, wherein the supports are round cylindrical supports.

* * * * *